(12) United States Patent
Husain

(10) Patent No.: US 9,096,561 B2
(45) Date of Patent: Aug. 4, 2015

(54) EPOXIDATION PROCESS

(71) Applicant: Scientific Design Company, Inc., Little Ferry, NJ (US)

(72) Inventor: Mansoor Husain, North Brunswick, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 14/253,366

(22) Filed: Apr. 15, 2014

(65) Prior Publication Data

US 2014/0309442 A1    Oct. 16, 2014

Related U.S. Application Data

(60) Provisional application No. 61/812,037, filed on Apr. 15, 2013.

(51) Int. Cl.
 *C07D 301/06*    (2006.01)

(52) U.S. Cl.
 CPC .................................. *C07D 301/06* (2013.01)

(58) Field of Classification Search
 CPC ..................................................... C07D 301/06
 USPC ......................................................... 549/532
 See application file for complete search history.

(56) References Cited

U.S. PATENT DOCUMENTS

| | | |
|---|---|---|
| 3,563,914 A | 2/1971 | Wattimena |
| 3,702,259 A | 11/1972 | Nielsen |
| 4,761,394 A | 8/1988 | Lauritizen |
| 4,766,105 A | 8/1988 | Lauritizen |
| 4,822,926 A | 4/1989 | Dye |
| 4,908,343 A | 3/1990 | Bhasin |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,171,868 A | 12/1992 | Albal et al. |
| 5,187,140 A | 2/1993 | Thorsteinson et al. |
| 5,407,888 A | 4/1995 | Herzog et al. |
| 5,503,813 A | 4/1996 | Evans |
| 6,187,973 B1 | 2/2001 | Husian |
| 7,615,654 B2 * | 11/2009 | Le-Khac et al. .............. 549/513 |
| 2007/0037991 A1 | 2/2007 | Rizkalla |
| 2009/0148361 A1 * | 6/2009 | Herman et al. ................. 423/22 |
| 2011/0152551 A1 | 6/2011 | Sachs et al. |

OTHER PUBLICATIONS

International Search Report and Written Opinion dated Aug. 27, 2014, received in a corresponding foreign application.
De Dardel, F., et al., "Ion Exchangers", Ullman's Encyclopedia of Industrial Chemistry, Published Online: Apr. 15, 2008.

* cited by examiner

*Primary Examiner* — T. Victor Oh
(74) *Attorney, Agent, or Firm* — Scully, Scott, Murphy & Presser, P.C.

(57) ABSTRACT

A method for the oxidation of ethylene to form ethylene oxide is provided that includes passing an aqueous stream through a guard bed and one or more ion exchange treatment beds. The guard bed and the aqueous stream contain from about 0.2 to 20 wt % ethylene glycol. The guard bed contains a crosslinked polystyrene resin, partially functionalized with quaternary ammonium functional groups and the resin has a surface area of greater than 400 m$^2$/g.

21 Claims, No Drawings

EPOXIDATION PROCESS

CROSS REFERENCE TO RELATED APPLICATION

This application claims benefit of U.S. Provisional Application Ser. No. 61/812,037, filed Apr. 15, 2013, the entire content of which is incorporated herein by reference.

FIELD OF THE INVENTION

The present invention relates to a method for the oxidation of ethylene into ethylene oxide.

BACKGROUND OF THE INVENTION

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2000 was about 15 billion tons. (About two thirds of the ethylene oxide produced is further processed into ethylene glycol, while about ten percent of manufactured ethylene oxide is used directly in applications such as vapor sterilization.)

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is, Ag-based epoxidation catalysts that are especially efficient at catalyzing the desired product reaction of ethylene and oxygen to ethylene oxide rather than the side reaction of ethylene and oxygen, which produces carbon dioxide byproduct (and water).

However, while high selectivity catalysts have reduced the formation of carbon dioxide byproduct they may also have increased the production of other undesired byproducts, notably aldehydic impurities such as acetaldehydes and formaldehydes and their associated acids. Acetaldehyde and formaldehyde have long been known as byproducts formed during the operation of ethylene oxide plants. Acetaldehyde is formed as a result of the isomerization of ethylene oxide, while formaldehyde is formed by the reaction of ethylene oxide with oxygen. The associated acids, acetic acid and formic acid, are produced by oxidizing acetaldehyde and formaldehyde, respectively.

While an impurity like carbon dioxide is produced almost exclusively on the catalyst bed in the EO reactor, acetaldehydes, formaldehydes and their associated acids are produced both on the catalyst and past the catalyst bed. Aldehydes and their associated acids can negatively affect the UV quality of the ethylene glycol solution and thereby cause degradation of fiber grade ethylene glycol product. Additionally, the formation of their associated acids (as well as their aldehydic reagents) can decrease the pH to levels sufficiently low to cause corrosion in the plant. These considerations are even more serious in plants that produce Fiber Grade MEG (monoethylene glycol).

One possible method of preventing or reducing the corrosion caused by acidic pH levels is to replace the carbon steel components with stainless steel components. However, this is not only extremely expensive but, at best, it only reduces the rate of corrosion rather than preventing the occurrence of corrosion. Moreover, this of course does not address the problem of low ethylene glycol product quality.

Another possible solution is disclosed in U.S. Pat. No. 4,822,926 in which the reactor product stream is supplied to a quench section (the quench section being disposed inside the EO absorber), and in the quench section the reactor product stream is contacted with a base-containing recirculating aqueous solution in order to neutralize the pH and eliminate some of the organics.

The addition of base like sodium hydroxide does reduce the pH (and as a consequence reduces or eliminates the corrosion in the plant) as well as prevent the formation of some of the organics and aldehydic impurities. But the addition of caustic also frequently causes the decomposition and degradation of the ethylene glycol product this is especially the case for heavier ethylene glycols like triethylene glycol, which often cannot be manufactured to meet minimum quality standards in a process utilizing caustic. Thus, in the end, caustic addition merely exchanges one problem (corrosion and impurity formation) for another (poor product quality).

Far better for eliminating aldehydic and other impurities from the cycle water are ion exchange resins such as those disclosed in U.S. Pat. No. 6,187,973. These ion exchange resins are extremely effective at removing the impurities from the cycle water, without causing the negative consequences mentioned above that result from caustic treatment.

While the use of ion exchange resins is far superior to other techniques, some difficulties with their use still exist. For example, certain organics such as long-chain hydrocarbons can damage the ion exchange resins. One such hydrocarbon species is long-chain esters, which are produced as a result of the build-up of aldehydic impurities and acids in the ethylene oxide as well as the glycol section. These aldehydic impurities then readily react with ethylene oxide and ethylene glycol to make a long-chain ester. For example, formic acid reacts with ethylene glycol to produce ethylene glycol monoformate, which can in turn successively react with more formic acid to produce heavier homologs (i.e., longer-chained hydrocarbons) of ethylene glycol monoformate.

Long-chain esters damage the ion exchange resins because although they are easily adsorbed onto the surface of the ion exchange resin, once adhered to the surface they become elution-resistant, i.e., they do not elute during regeneration meaning that they remain "trapped" on the surface of the ion exchange resin. This reduces the capacity of the ion exchange resin which in turn requires more frequent regeneration cycles. Moreover, the presence of these impurities may also cause resin swelling which can slow the flow of reactants through the ion exchange resin, reducing its throughput.

Hitherto, there has been no technique available for dealing with these long-chain hydrocarbons and the damage they do to ion exchange resins. Instead, the efforts of investigators have focused on techniques for reducing impurities in glycol solutions using ion exchange resins and overlooked that, in the course of performing their function, ion exchange resins often become damaged by continually adsorbing elution-resistant long-chain hydrocarbons. These damaged ion exchange resins are then much less effective at removing impurities and require more frequent regeneration.

Given the foregoing there is a continuing need in the art to reduce the damage to the ion exchange resins caused by these elution-resistant impurities, which become trapped on the surface of the ion exchange resin and do not readily elute during regeneration.

BRIEF SUMMARY OF THE INVENTION

The present invention relates to a method for the oxidation of ethylene to form ethylene oxide which comprises passing an aqueous stream through a guard bed and one or more ion exchange treatment beds; the guard bed and the aqueous stream containing from about 0.2 to 20 wt % ethylene glycol, the guard bed containing a cross-linked polystyrene resin, partially functionalized with quaternary ammonium functional groups and the resin having a surface area of greater than 400 $m^2/g$.

DETAILED DESCRIPTION OF THE INVENTION

All parts, percentages and ratios used herein are expressed by volume unless otherwise specified. All documents cited herein are incorporated by reference.

By "long-chain hydrocarbon" it is meant any aliphatic hydrocarbon whose parent hydrocarbon chain has four or more carbons.

By "solid adsorbent resin" it is meant the resin prepared according to the present invention.

By "ion exchange resin" it is meant any conventional ion exchange resin, as known to a skilled person and, which is a readily-available article of commerce.

It has been found in the present invention that the damage to the ion exchange resins caused by elution-resistant impurities can be reduced or eliminated by the installation of a guard bed upstream from the ion exchange resin. This guard bed comprises a solid adsorbent resin that adsorbs long-chain hydrocarbons and then readily elutes the long-chain aliphatic hydrocarbons during regeneration in contrast to ion exchange resins which adsorb but do not elute the long-chain hydrocarbons.

Without being limited by theory, it is believed that the difficulty that conventional ion exchange resins have in eluting long-chain hydrocarbons (e.g., an aldehyde-derived long-chain ester like ethylene glycol monoformate) during regeneration can be ascribed to the weakly polar, largely non-ionic nature of the long-chain hydrocarbons themselves. Because these long-chain hydrocarbons are only weakly-polar, the ionic functional group active sites of the ion exchange resin only partially trap these long-chain hydrocarbons instead, most of the adsorption of the long-chain hydrocarbon happens by the physical entanglement and penetration of the long-chain hydrocarbon into the fibers and pores of the ion exchange resin. Thus, during a typical regeneration cycle, for example when an anion-exchange resin is regenerated with caustic, the long-chain hydrocarbon does not readily elute into the caustic, because the caustic regenerant targets the functional group active sites seeking to replace the trapped anions at those sites with $OH^-$ ions. But this is ineffectual, because adsorption has occurred not at the functional groups but at random locations on the surface of the resin where the long-chain hydrocarbon has inserted itself into the resin or into the pores of the resin.

The solid adsorbent resin of the present invention is similar to conventional ion exchange resins in that it uses physical adsorption of the long-chain hydrocarbons into the pores of the solid adsorbent resin in order to trap and adsorb the long-chain hydrocarbons. However, the pores of the solid adsorbent resins are much larger than the pores in ion exchange resins. Unlike in the ion exchange resin where the small pores hold the long-chain hydrocarbon tightly and it becomes impossible to release during regeneration, the much larger pores of the solid adsorbent resin hold the long-chain hydrocarbon much more weakly, and during regeneration, the long-chain hydrocarbons are easily rinsed out of these large pores allowing for an extremely high regeneration efficiency.

The use of this invention will now be described below in greater detail, below, as a component of an ethylene oxide production process.

Ethylene oxide is produced by continuously contacting an oxygen-containing gas with an olefin, preferably ethylene, in the presence of an ethylene oxide ("epoxidation") catalyst (described in greater detail below). Oxygen may be supplied to the reaction in substantially pure molecular form or in a mixture such as air. By way of example, typical reactant feed mixtures under operating conditions may contain from about 0.5% to about 45%, preferably about 5% to about 30% of ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. Carbon dioxide and water are byproducts of the epoxidation process as well as common contaminants in the feed gases. Both have adverse effects on the catalyst, so the concentrations of these components are usually kept at a minimum.

Also present in the reaction, as previously mentioned, are one or more chloride moderators, non-limiting examples of which include organic halogen-containing compounds such as $C_1$ to $C_8$ halohydrocarbons; especially preferred are chloride-containing moderators such as methyl chloride, ethyl chloride, ethylene dichloride, vinyl chloride or mixtures thereof. Controlling chloride concentration level is particularly important with rhenium-containing catalysts.

As mentioned above, a usual method for the ethylene epoxidation process comprises the vapor-phase oxidation of ethylene with molecular oxygen, in the presence of an epoxidation catalyst, in a fixed-bed tubular reactor. Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long, each filled and packed with catalyst. The reaction feed mixture (described above) is introduced into these tubes, and the resulting reactor effluent gas contains ethylene oxide, un-used reactants, and byproducts.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 to about 20 seconds.

The reactor effluent exits through the reactor outlet, is cooled and flows to the EO scrubbing column, where the reactor effluent is contacted with recirculated lean cycle water to absorb the ethylene oxide from the reactor effluent. These scrubbing column liquids (rich cycle water) are then fed to the EO stripping column for the recovery of the ethylene oxide. In the EO stripping column the ethylene oxide is stripped out and the ethylene oxide vapor is sent overhead to a second EO absorber. The water in the stripping column (the lean cycle water, which is an aqueous stream comprising 0.2 to 20 wt % ethylene glycol) flows through the stripping column bottoms and a bleed stream is taken from the lean cycle water before the lean cycle water is returned to the EO scrubber where it is used to absorb ethylene oxide. This bleed stream is sent to a lean cycle water treatment unit.

The lean cycle water treatment unit includes a guard bed placed upstream from one or more ion exchange treatment beds, each ion exchange treatment bed being arranged in series with respect to the others. Each ion exchange treatment bed may contain either a cation resin or anion resin. Any suitable cation- or anion-exchange resin may be used. For a more comprehensive description of cation- and anion-exchange resins see, de Dardel, F. and Arden, T. V. 2008. *Ion Exchangers* in *Ullman's Encyclopedia of Industrial Chemistry*. Examples of suitable cation-exchangers include the Tulsion T56MP and TG 057 cation exchanger from Thermax LTD, Pune, India; or Amberlyst A15 MP, from Rohm and Haas, Philadelphia, Pa. Suitable anion-exchangers are disclosed in greater detail in U.S. Pat. No. 6,187,973. Examples of suitable anion-exchangers include, Tulsion A8X MP and A9X MP anion exchangers from Thermax LTD.

The guard bed contains a solid adsorbent resin prepared according to the present invention. The solid adsorbent resin comprises a cross-linked polystyrene matrix with a quaternary ammonium functional group. The cross-linked polystyrene resin is converted to the quaternary ammonium form by: (1) preparing a chloromethylated polystyrene by treating the cross-linked polystyrene resin with chloromethyl methyl ether over an appropriate catalyst; and then (2) replacing the chlorine in the chloromethylated group with an amine or ammonia to provide a quaternary ammonium functional group on the cross-linked polystyrene matrix. The resin is then subjected to finishing and refinement procedures. The final resin has very large pores and thus a very high surface area greater than 400 $m^2/g$, preferably greater than 600 $m^2/g$, more preferably greater than 800 $m^2/g$, even more preferably greater than 1000 $m^2/g$. The resin is preferably hydrophobic.

Preferably, by step (2), above, the solid adsorbent resin is only partially functionalized; more preferably, the solid adsorbent resin is substantially free of functional groups. Even more preferably the solid adsorbent resin contains no detectable or measurable functional groups.

In one embodiment, the resin is a polystyrene-divinylbenzene resin.

Thermax's Tulsion ASD 057 resin is a suitable solid adsorbent resin for use in the present invention.

In operation, an aqueous ethylene glycol solution containing impurities such as formaldehyde, acetaldehyde and their associated acids as well as the long-chain hydrocarbons and other organics is contacted with the solid adsorbent resin of the present invention and the concentration of these impurities in the aqueous ethylene glycol solution is reduced as the impurities are adsorbed on the surface of the solid absorbent resin. The solid adsorbent resin has a high selectivity for the long-chain hydrocarbons and relatively low selectivity for ionic impurities. This selectivity difference is to prevent the solid adsorbent resin from having its active adsorbing sites (primarily the large pores) from being filled up with ionic impurities which can be easily handled by the ion exchange resins in the ion exchange treatment beds; this selectivity difference allows nearly all of the available capacity of the solid adsorbent resin to be used for adsorbing long-chain hydrocarbons.

With the addition of the guard bed containing the solid adsorbent resin of the present invention, the concentration of the long-chain hydrocarbons in the lean cycle water when the lean cycle water reaches the ion exchange treatment bed is reduced to zero or close to zero. This protects the ion exchange resins from being damaged by the long-chain hydrocarbons and increases the amount of solution which can be treated before regeneration is necessary. This reduces the frequency with which the ion exchange resins need to be regenerated, improving process efficiency. And it also lengthens the service life of the ion exchange resins, allowing them to be used for much longer periods of time before they must be discarded and replaced with new ion exchange resins.

Generally speaking, the aqueous ethylene glycol-containing solutions (i.e., the lean cycle water) treated in accordance with the invention comprise about 0.2 to 20 wt % ethylene glycol, about 80 to 99.7 wt % water and about 100 ppm to 1.0 wt % impurities. The ethylene glycol solution is contacted with this ion exchange resin at temperatures of from about 30° C. to 50° C. although higher or lower temperatures may be used. Atmospheric pressure is preferred but higher pressures can also be used depending on whether a pressure differential in the next processing unit is desired. Illustrative flow rates are about 1 to 10 volumes of solution per volume of resin per hour although this can vary widely.

The performance of the ion exchange resins in removing the impurities is continuously monitored by online measurement of the UV transmittance. The UV transmittance is a measurement of the concentration of the impurities in the aqueous ethylene glycol solution. If the aqueous ethylene glycol solution fails to meet certain minimum UV transmittance percentages, then it will be of insufficient quality to quality as fiber grade and hence the value of it as ethylene glycol will be much reduced. The minimum UV transmittance rates are as follows:

TABLE I

| Wave Length (nm) | Transmittance %, min |
|---|---|
| 220 | 80 |
| 275 | 85 |
| 350 | 99 |

When the UV transmittance of the treated aqueous ethylene glycol solution starts to approach these minimum values, this indicates that the capacity of the ion exchange resins of the lean cycle water treatment unit to adsorb impurities from the aqueous ethylene glycol solution has been reached and it needs to be regenerated.

Having been treated in the lean cycle water treatment unit, the treated water is sent to the glycol section of the plant, where the ethylene glycol is separated from the treated water (and the glycol purified) and the now glycol-free water sent as recycle water to the glycol reactors.

Regeneration occurs by washing the solid adsorbent and ion exchange resins with a regenerant. For convenience, any regenerants for use with ion exchange resins are suitable, but sodium hydroxide regenerate is especially preferred. During regeneration, the impurities, especially long-chain esters and other organics elute and are released during regeneration into the liquid regenerant.

For purposes of illustration only, the following are conditions that are often used in current commercial ethylene oxide reactor units: a gas hourly space velocity (GHSV) of 1500-10,000 h$^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof.

Silver-Based Epoxidation Catalyst

The silver-based epoxidation catalyst includes a support, and at least a catalytically effective amount of silver or a silver-containing compound; also optionally present is a promoting amount of rhenium or a rhenium-containing compound; also optionally present is a promoting amount of one or more alkali metals or alkali-metal-containing compounds. The support employed in this invention may be selected from a large number of solid, refractory supports that may be porous and may provide the preferred pore structure. Alumina is well known to be useful as a catalyst support for the epoxidation of an olefin and is the preferred support.

Regardless of the character of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles will preferably have equivalent diameters in the range from about 3 mm to about 12 mm, and more preferably in the range from about 5 mm to about 10 mm (Equivalent diameter is the diameter of a sphere having the same external surface (i.e., neglecting surface within the pores of the particle) to volume ratio as the support particles being employed.) Suitable supports are available from Saint-Gobain Norpro Co., Sud Chemie AG, Noritake Co., CeramTec AG, and Industrie Bitossi S.p.A. Without being limited to the specific compositions and formulations contained therein, further information on support compositions and methods for making supports may be found in U.S. Patent Publication No. 2007/0037991.

In order to produce a catalyst for the oxidation of an olefin to an olefin oxide, a support having the above characteristics is then provided with a catalytically effective amount of silver on its surface. The catalyst is prepared by impregnating the support with a silver compound, complex or salt dissolved in a suitable solvent sufficient to cause deposition of a silver-precursor compound onto the support. Preferably, an aqueous silver solution is used.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

As used herein the term "promoting amount" of a certain component of the catalyst refers to an amount of that component that works effectively to improve the catalytic performance of the catalyst when compared to a catalyst that does not contain that component. The exact concentrations employed, of course, will depend on, among other factors, the desired silver content, the nature of the support, the viscosity of the liquid, and solubility of the particular compound used to deliver the promoter into the impregnating solution. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

Suitable alkali metal promoters may be selected from lithium, sodium, potassium, rubidium, cesium or combinations thereof, with cesium being preferred, and combinations of cesium with other alkali metals being especially preferred. The amount of alkali metal deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 to 8 hours at a temperature of from 100° C. to 375° C., usually for duration of from about 0.5 to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Further information on catalyst manufacture may be found in the aforementioned U.S. Patent Publication No. 2007/0037991.

EXAMPLES

The invention will now be described in more detail with respect to the following non-limiting examples.

In Example 1a, a lean cycle water treatment unit containing a cation resin (Tulsion TG057+) and an anion resin (Tulsion A9X) were placed in series (with the cation resin upstream) and tested for their ability to remove impurities from a solution steam. These resins reached their capacity (based on the UV measurements specified in Table I) and required regeneration after 258 volumes of solution per volume of resin had been treated.

In Example 1b, a lean cycle water treatment unit containing the same cation resin (Tulsion TG057+) and an anion resin (Tulsion A9X) and were placed in series (with the cation resin upstream) but in this example, a Guard Bed containing Tulsion ASD 057-resin was placed upstream of these ion exchange units. In this example, the resins reached their capacity after 450 volumes of solution per volume of resin had been treated.

A comparison of Example 1a and 1b demonstrates that with the addition of the guard bed containing the solid adsorbent resin prepared according to the present invention, the amount of solution that can be treated before regeneration is necessary increases significantly.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

What I claim is:

1. A method for the oxidation of ethylene to form ethylene oxide which comprises:
   passing an aqueous stream through a guard bed and one or more ion exchange treatment beds, wherein said guard bed and said aqueous stream contain from about 0.2 to 20 wt % ethylene glycol, and wherein said guard bed contains a cross-linked polystyrene resin, partially functionalized with quaternary ammonium functional groups and said resin has a surface area of greater than 400 $m^2/g$.

2. The method according to claim 1, wherein said resin of said guard bed is hydrophobic.

3. The method according to claim 1, wherein said one or more ion exchange treatment beds contain resins selected from the group consisting of cationic exchange resins and anionic exchange resins.

4. The method according to claim 1, further comprising initiating an epoxidation reaction by reacting a feed gas composition containing ethylene and oxygen in the presence of an epoxidation catalyst containing a promoting amount of rhenium.

5. The method according to claim 1, wherein said guard bed is located upstream from said one or more ion exchange treatment beds.

6. The method according to claim 5, wherein said one or more ion exchange treatment beds are arranged in series with respect to each other.

7. The method according to claim 1, wherein said aqueous stream further comprises an aliphatic hydrocarbon whose parent hydrocarbon chain has four or more carbon atoms.

8. The method according to claim 7, wherein said aliphatic hydrocarbon is absorbed by said resin of said guard bed.

9. The method according to claim 8, further comprises regenerating said resin by releasing said absorbed aliphatic hydrocarbon from said resin of said guard bed.

10. The method according to claim 9, wherein said regenerating comprises contacting said resin of said guard bed containing said absorbed aliphatic hydrocarbon with a regenerate.

11. The method according to claim 10, wherein said regenerate is sodium hydroxide.

12. The method according to claim 7, wherein said aqueous solution reaching said one or more ion exchange treatment beds contains zero or near zero of said aliphatic hydrocarbon.

13. The method according to claim 1, wherein said resin of said guard bed comprises polystyrene-divinylbenzene.

14. The method according to claim 1, wherein said surface area of said resin of said guard bed is greater than 1000 $m^2/gm$.

15. The method according to claim 1, wherein said aqueous stream further includes water, aldehydic impurities, aldehydic acid impurities, and an aliphatic hydrocarbon impurity whose parent hydrocarbon chain has four or more carbon atoms.

16. The method according to claim 15, wherein said aqueous stream contains from 80 to 99.7 weight percent of said water, and from about 100 ppm to 1.0 weight percent of said impurities.

17. The method according to claim 1, wherein said resin of said guard bed is obtained by:

preparing a chloromethylated polystyrene by treating a cross-linked polystyrene resin with chloromethyl methyl ether over a silver-based epoxidation catalyst; and replacing the chloromethylated group with an amine or ammonia.

18. A method comprising:

reacting ethylene with oxygen in the presence of an epoxidation catalyst and in a fixed-bed reactor to provide a reactor effluent containing at least ethylene oxide;

removing said reactor effluent containing at least ethylene oxide from said reactor by passing said reactor effluent through a reactor outlet of said fixed-bed reactor;

flowing said reactor effluent to an ethylene oxide scrubbing column to provide scrubbing column liquids, wherein said reactor effluent in said ethylene oxide scrubber column is contacted with recirculated lean cycle water to absorb said ethylene oxide from said reactor effluent;

feeding said ethylene oxide scrubbing column liquids to an ethylene oxide stripping column to recover said ethylene oxide; and passing an aqueous stream exiting said ethylene oxide stripping column through a guard bed and one or more ion exchange treatment beds, wherein said guard bed and said aqueous stream contain from about 0.2 to 20 wt % ethylene glycol, and wherein said guard bed contains a cross-linked polystyrene resin, partially functionalized with quaternary ammonium functional groups and said resin has a surface area of greater than 400 $m^2/g$.

19. The method of claim 1 wherein said resin has a surface area of greater than 600 $m^2/g$.

20. The method of claim 1 wherein said resin has a surface area of greater than 800 $m^2/g$.

21. The method of claim 1 wherein said resin has a surface area of greater than 1000 $m^2/g$.

* * * * *